(12) United States Patent
Guzman

(10) Patent No.: US 12,345,526 B2
(45) Date of Patent: Jul. 1, 2025

(54) TOOL FOR MEASURING DISTANCE

(71) Applicant: Sea Ray Construction LLC, Rumson, NJ (US)

(72) Inventor: Raymond Guzman, Rumson, NJ (US)

(73) Assignee: Sea Ray Construction LLC, Rumson, NJ (US)

( * ) Notice: Subject to any disclaimer, the term of this patent is extended or adjusted under 35 U.S.C. 154(b) by 529 days.

(21) Appl. No.: 17/743,660

(22) Filed: May 13, 2022

(65) Prior Publication Data

US 2022/0361771 A1   Nov. 17, 2022

Related U.S. Application Data

(60) Provisional application No. 63/188,925, filed on May 14, 2021.

(51) Int. Cl.
*G01B 5/06* (2006.01)
(52) U.S. Cl.
CPC ................... *G01B 5/061* (2013.01)
(58) Field of Classification Search
CPC ........ G01B 5/061; G01B 3/08; G01B 3/1092; A61B 5/1072
See application file for complete search history.

(56) References Cited

U.S. PATENT DOCUMENTS

| | | | | |
|---|---|---|---|---|
| 1,105,439 | A * | 7/1914 | Jensen | A41H 1/02 33/8 |
| 3,248,797 | A * | 5/1966 | Selleck | G01C 5/00 33/367 |
| 3,680,214 | A * | 8/1972 | Quenot | G01B 3/08 33/759 |
| 4,202,108 | A * | 5/1980 | Adams, Jr. | E04F 21/1838 33/379 |

(Continued)

FOREIGN PATENT DOCUMENTS

| | | | |
|---|---|---|---|
| CN | 211503974 U | * | 9/2020 |
| GB | 1464535 | | 2/1977 |

(Continued)

OTHER PUBLICATIONS

International Search Report & Written Opinion for Application No. PCT/US2022/029189 dated Sep. 15, 2022, 11 pages.

(Continued)

*Primary Examiner* — Yaritza Guadalupe-McCall
(74) *Attorney, Agent, or Firm* — MOSER TABOADA

(57) ABSTRACT

Embodiments of tools for measuring a vertical height are provided herein. In some embodiments, a tool for measuring a vertical height includes: a first elongate member having a measurement tape; a handle coupled to the first elongate member; and a second elongate member slidingly coupled to the first elongate member, wherein the second elongate member includes a measurement window configured to facilitate reading of the measurement tape to indicate a (Continued)

length of the tool between an upper end of the first elongate member and a lower end of the second elongate member, wherein the handle is disposed between the measurement window and the lower end of the second elongate member when the tool is in a retracted position and configured to move the first elongate member with respect to the second elongate member.

18 Claims, 7 Drawing Sheets

(56) References Cited

U.S. PATENT DOCUMENTS

| | | | | |
|---|---|---|---|---|
| 4,228,588 | A * | 10/1980 | Horton, Jr. | G01C 15/00 33/1 H |
| 4,649,652 | A * | 3/1987 | Dickinson | B25H 7/04 D10/64 |
| 5,038,493 | A * | 8/1991 | Stabs | G01B 5/061 33/809 |
| 5,070,620 | A | 12/1991 | Crain et al. | |
| 5,317,813 | A * | 6/1994 | Reed | G01B 3/08 33/809 |
| 5,915,810 | A | 6/1999 | Cameron | |
| 6,085,434 | A | 7/2000 | Mitchell | |
| 6,418,631 | B1 | 7/2002 | Ramsthaler | |
| 6,820,342 | B2 * | 11/2004 | Ramsthaler | B43K 23/00 33/809 |
| 6,931,747 | B2 * | 8/2005 | Rego | A41H 1/04 177/245 |
| 8,096,061 | B2 * | 1/2012 | Biselx | G01B 5/008 33/832 |
| 8,756,820 | B2 * | 6/2014 | Bartolini | A41H 1/04 33/8 |
| 10,495,434 | B1 * | 12/2019 | Motz | G01B 3/20 |
| 10,690,471 | B1 * | 6/2020 | DuFaux | G01B 3/08 |
| 2002/0017028 | A1 * | 2/2002 | Wishart | G01C 15/004 33/286 |
| 2009/0106993 | A1 | 4/2009 | McKenna et al. | |
| 2010/0287786 | A1 * | 11/2010 | Biselx | G01B 5/008 33/832 |
| 2012/0023764 | A1 * | 2/2012 | Bartolini | A41H 1/04 33/8 |
| 2013/0152415 | A1 | 6/2013 | Yi et al. | |
| 2022/0361771 | A1 * | 11/2022 | Guzman | G01B 5/061 |

FOREIGN PATENT DOCUMENTS

| | | | | |
|---|---|---|---|---|
| JP | | 2016114531 A | * | 6/2016 |
| WO | WO-2022241213 A1 | * | 11/2022 | A61B 5/1072 |

OTHER PUBLICATIONS

Extended European Search Report for Application No. 22808404.2 dated Jul. 30, 2024, 7 pages.

* cited by examiner

TOOL FOR MEASURING DISTANCE

CROSS-REFERENCE TO RELATED APPLICATIONS

This application claims benefit of U.S. Provisional Patent Application Ser. No. 63/188,925, filed May 14, 2021, which is herein incorporated by reference in its entirety.

FIELD

Embodiments of the present disclosure relate to measuring tools for carpentry, and more specifically, a rigid extendable measuring tool.

BACKGROUND

Carpenters commonly use measuring tools while performing construction work. A conventional measuring tool is a tape measure. Tape measures typically have a flexible metal strip with measurement markings rolled into a housing. In use, the flexible metal strip extends out from the housing to perform a measurement and subsequently retracts back into the housing for storage. For vertical measurements, for example, when measuring studs to build a wall, the flexible metal strip may be difficult to control and may provide inaccurate measurements due to bending of the flexible metal strip, particularly when measuring longer distances. In addition, taking vertical height measurements with a measure tape may be time consuming, especially when tens or even hundreds of such measurements are required for a given construction project.

Therefore, the inventor has provided embodiments of an improved measuring tool for vertical measurements.

SUMMARY

Embodiments of tools for measuring a vertical height are provided herein. In some embodiments, a tool for measuring a vertical height includes: a first elongate member having a measurement tape; a handle coupled to the first elongate member; and a second elongate member slidingly coupled to the first elongate member, wherein the second elongate member includes a measurement window configured to facilitate reading of the measurement tape to indicate a length of the tool between an upper end of the first elongate member and a lower end of the second elongate member, wherein the handle is disposed between the measurement window and the lower end of the second elongate member when the tool is in a retracted position and configured to move the first elongate member with respect to the second elongate member.

In some embodiments, a tool for measuring a vertical height includes: a first elongate member having one or more channels disposed along an elongate axis; a handle coupled to the first elongate member; and a second elongate member slidingly coupled to the first elongate member via the one or more channels, wherein the second elongate member includes a measurement window on a front side of the second elongate member configured to facilitate reading of a measurement tape to indicate a length of the tool between an upper end of the first elongate member and a lower end of the second elongate member and a clamp to selectively lock or unlock the second elongate member with respect to the first elongate member, wherein the handle is configured to raise the first elongate member with respect to the second elongate member.

In some embodiments, a tool for measuring a vertical height includes: a first elongate member having one or more channels along an elongate axis; a handle coupled to the first elongate member; and a second elongate member slidingly coupled to the first elongate member via the one or more channels, wherein the second elongate member includes a measurement window disposed about 4.0 to about 7.5 feet from a lower end of the second elongate member and configured to facilitate reading of a measurement tape to indicate a length of the tool between an upper end of the first elongate member and the lower end of the second elongate member and a clamp to selectively lock or unlock the second elongate member with respect to the first elongate member, wherein the handle is disposed between the measurement window and the lower end of the second elongate member and configured to raise the first elongate member with respect to the second elongate member.

Other and further embodiments of the present disclosure are described below.

BRIEF DESCRIPTION OF THE DRAWINGS

Embodiments of the present disclosure, briefly summarized above and discussed in greater detail below, can be understood by reference to the illustrative embodiments of the disclosure depicted in the appended drawings. However, the appended drawings illustrate only typical embodiments of the disclosure and are therefore not to be considered limiting of scope, for the disclosure may admit to other equally effective embodiments.

Figure 1:
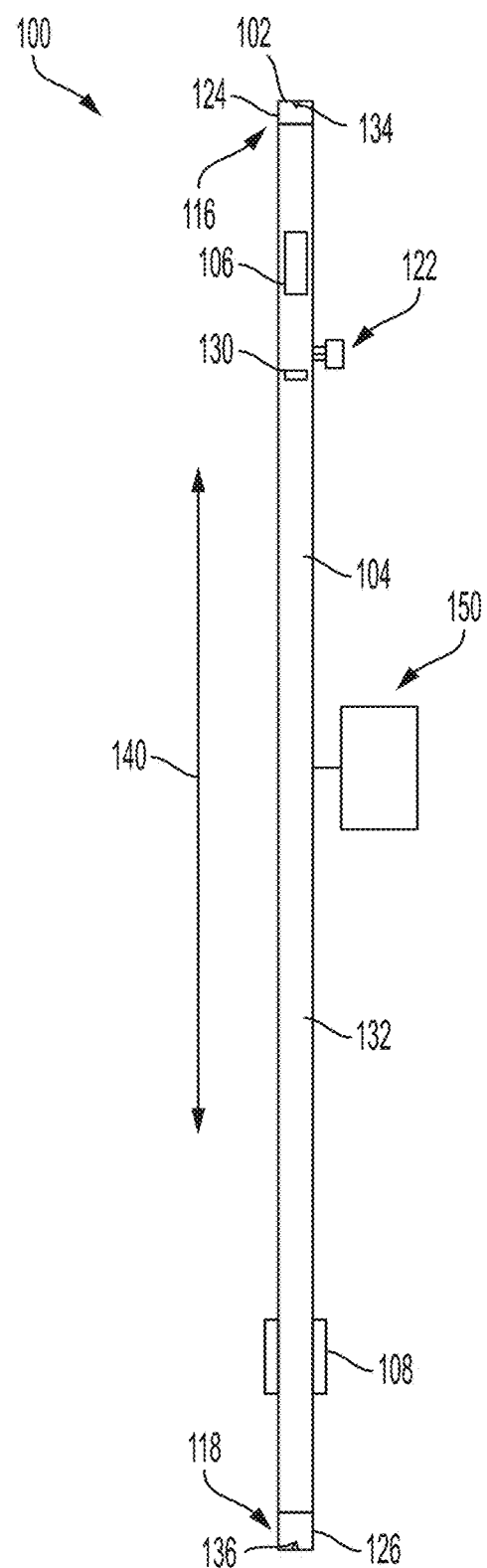
FIG. 1 depicts a front view of a tool for measuring a vertical height in accordance with some embodiments of the present disclosure.

To facilitate understanding, identical reference numerals have been used, where possible, to designate identical elements that are common to the figures. The figures are not drawn to scale and may be simplified for clarity. Elements and features of one embodiment may be beneficially incorporated in other embodiments without further recitation.

DETAILED DESCRIPTION

Embodiments of a measuring tool for vertical measurements are provided herein. The measuring tool generally includes multiple elongate members that are slidingly engaged via or within a channel of one of the elongate members. The measuring tool may be expanded by raising the multiple elongate members with respect to each other to make a vertical measurement. The elongate members are advantageously rigid, allowing for accurate vertical measurements. The elongate members that are configured to be raised include a handle for ease of raising and/or adjusting position of the elongate members. The handle is positioned at a location to advantageously prevent user fatigue. For example, the handle may be positioned so that a user's hand remains at or below shoulder level when the measuring tool is raised.

Figure 2:
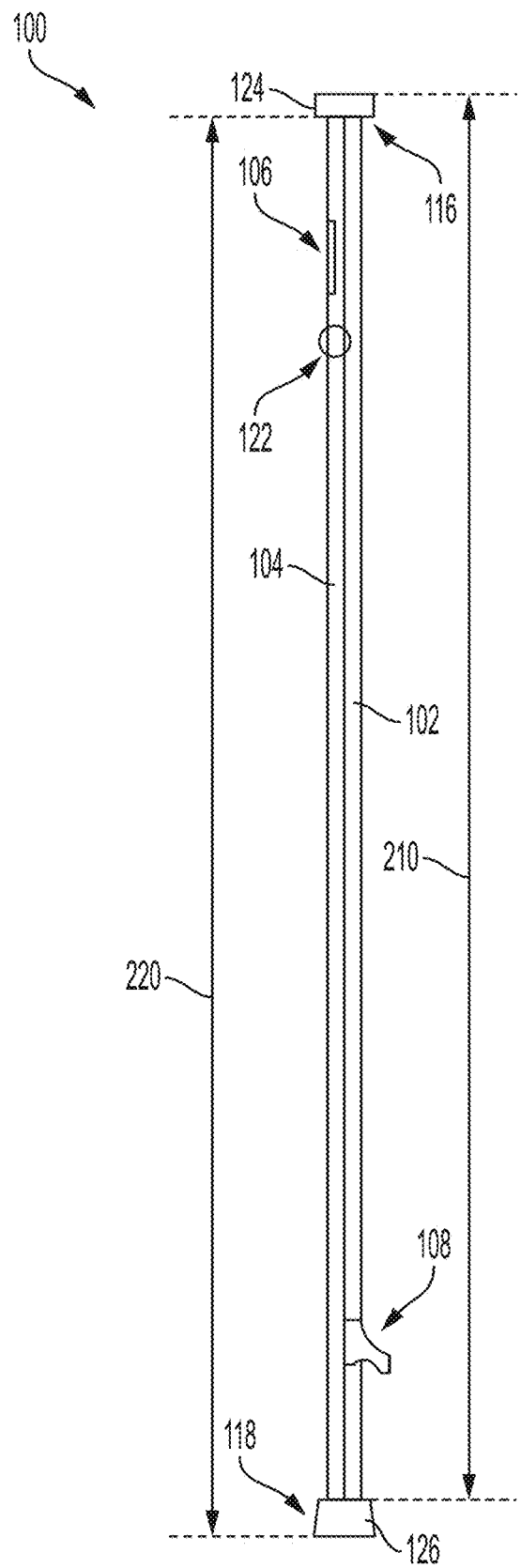
FIG. 2 depicts a right-side view of a tool for measuring a vertical height in accordance with some embodiments of the present disclosure.

FIG. 1 depicts a front view of a measuring tool (e.g., tool 100) for measuring a vertical height in accordance with some embodiments of the present disclosure. FIG. 2 depicts a right-side view of a tool for measuring a vertical height in accordance with some embodiments of the present disclosure. The tool 100 generally comprises a first elongate member 102 and a second elongate member 104 slidingly coupled to the first elongate member 102. In some embodiments, a handle 108 is coupled to the first elongate member 102 to assist in raising and/or adjusting the position of the first elongate member 102 with respect to the second elongate member 104. FIGS. 1 and 2 depict the tool 100 in a retracted position. When the first elongate member 102 is raised with respect to the second elongate member 104 along an elongate axis 140, the tool 100 is in a measuring position. In some embodiments, the first elongate member 102 is not a tubular element.

The first elongate member 102 slidingly coupled to the second elongate member 104 in a non-telescoping configuration advantageously prevents user fatigue. A telescoping configuration requires the user's hand to be frequently raised above shoulder level. A telescoping configuration also requires multiple up and down motion of the user's hand and arm to expand a tool to take one measurement and additional up and down motion of the user's hand and arm to retract the tool. The handle 108 coupled to the first elongate member 102 allows for a single upward motion of the user's hand and arm to take one measurement. The sliding engagement of the first elongate member 102 and the second elongate member 104 provides a low friction engagement for ease of adjusting. Also, the weight of the first elongate member 102 can operate to lower the first elongate member when upward force provided by the user's hand or arm is removed or sufficiently lessened. As such, the sliding engagement between the first elongate member 102 and the second elongate member 104 facilitates the making of quick measurements and moving to the next measurement.

In some embodiments, the first elongate member 102 has a first height 210 of about 4 to about 7 feet. In some embodiments, the second elongate member 104 has a second height 220 of about 4 to about 7 feet. The first elongate member 102 and the second elongate member 104 are made of a suitable rigid material. For example, in some embodiments, the suitable rigid material comprises essentially of a metal material, a ceramic material, a polymer material, a combination thereof, or the like. In some embodiments, the suitable rigid material comprises an organic material such as wood, bamboo, or the like. In some embodiments, the first elongate member 102 includes a head 124 at the upper end 116 of the first elongate member 102. In some embodiments, the head 124 may be made of a material different than the first elongate member 102. In some embodiments, the head 124 is made of polymer or rubber to provide a durable and replaceable contact surface. The head 124 may be made of a high friction material to enhance stability and prevent sliding of the tool 100 during measurements. In some embodiments, the head 124 may include a center notch 134 for pin point measurements.

In some embodiments, the second elongate member 104 includes a foot 126 at a lower end 118 of the second elongate member 104. In some embodiments, the foot 126 may be made of a material different than the second elongate member 104. In some embodiments, the foot 126 is made of polymer or rubber to provide a durable and replaceable contact surface. The foot 126 may be made of a high friction material to enhance stability and prevent sliding of the tool 100 during measurements. In some embodiments, the foot 126 may include a center notch 136 for pin point measurements.

Figure 7:
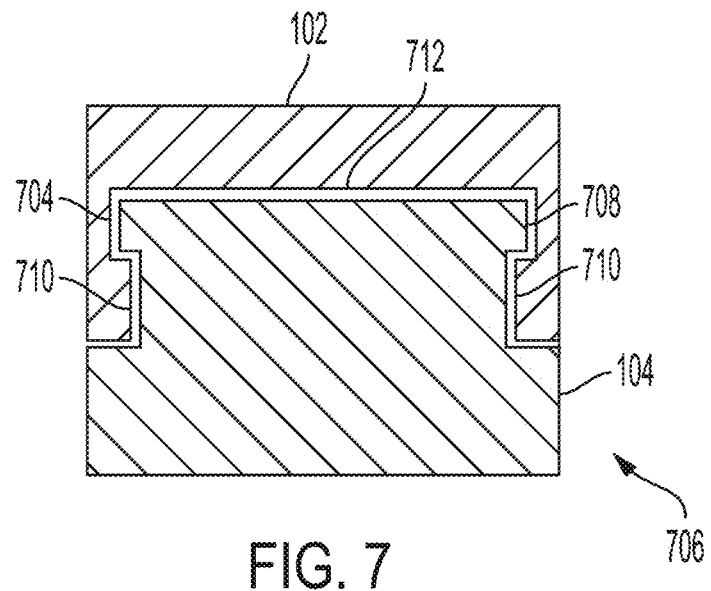
FIG. 7 depicts a cross-sectional top view of a tool for measuring a vertical height in accordance with some embodiments of the present disclosure.

FIG. 7 depicts a cross-sectional top view of a tool for measuring a vertical height in accordance with some embodiments of the present disclosure. In some embodiments, the first elongate member 102 is not a tubular element. In some embodiments, the second elongate member 104 is not a tubular element. One of the first elongate member 102 or the second elongate member 104 generally includes a channel for the other of the first elongate member 102 or the second elongate member 104 to slidingly engage with. For example, as shown in FIG. 7, the first elongate member 102 has a channel 704 disposed along the elongate axis 140 of the first elongate member 102. In some embodiments, the channel 704 is an inverted T-shaped channel. In some embodiments, the second elongate member 104 has a T-shaped cross-sectional shape and configured to slidingly engage with the inverted T-shaped channel. The T-shaped cross-sectional shape generally comprises a member head 706 and a member foot 708 that is narrower than the member head 706. The first elongate member 102 may include one or more tabs 710 that extend into the channel 704 to facilitate retaining the second elongate member 104 via or within the channel 704. In some embodiments, a back surface 712 of the channel 704 is substantially planar.

Figure 9:
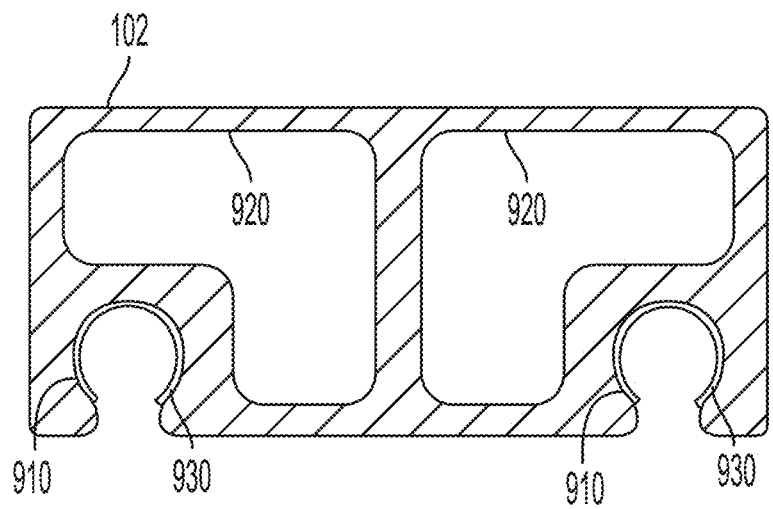
FIG. 9 depicts a cross-sectional top view of a first elongate member in accordance with some embodiments of the present disclosure.
Figure 10:
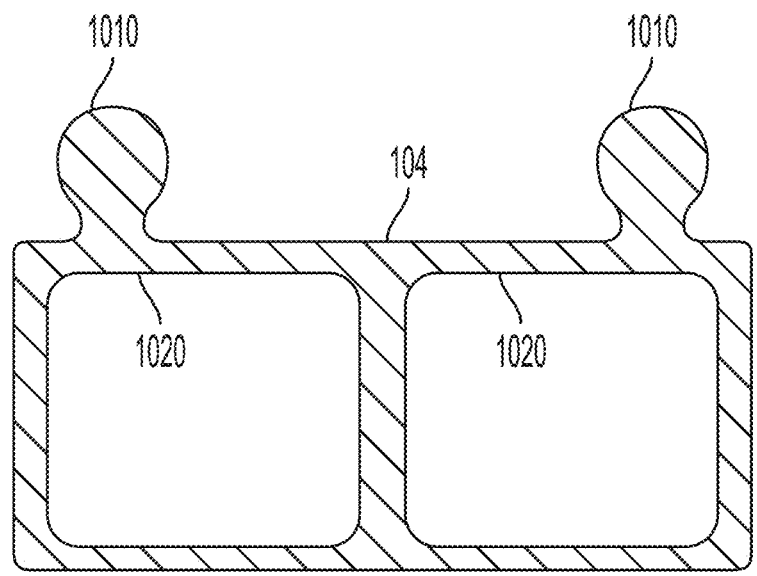
FIG. 10 depicts a cross-sectional top view of a second elongate member in accordance with some embodiments of the present disclosure.

In another example, FIG. 9 depicts a cross-sectional top view of a first elongate member in accordance with some embodiments of the present disclosure, and FIG. 10 depicts a cross-sectional top view of a second elongate member in accordance with some embodiments of the present disclosure. In some embodiments, the first elongate member 102 includes one or more channels 910 along the elongate axis 140. In some embodiments, the one or more channels 910 are two channels. In some embodiments, the one or more channels 910 have rounded cross-sectional shapes, although other cross-sectional shapes may also be used. In some embodiments, the second elongate member 104 includes one or more protrusions 1010 along the elongate axis 140 corresponding with the one or more channels 910 such that when the one or more protrusions 1010 are disposed in the one or more channels 910, the first elongate member 102 and the second elongate member 104 may be slidingly coupled together. In some embodiments, the one or more channels 910 may include inserts 930 to facilitate smoother gliding between the first elongate member 102 and the second elongate member 104. The inserts 930 may generally take the shape of the one or more protrusions 1010 for facilitating smoother gliding. In some embodiments, the inserts 930 are made of plastic, such as ultra-high molecular weight polyethylene.

The first elongate member 102 may include one or more voids 920. The one or more voids 920 may advantageously reduce the weight of the first elongate member 102. The second elongate member 104 may include one or more voids 1020. The one or more voids 1020 may advantageously reduce the weight of the second elongate member 104. In some embodiments, a wall thickness between the one or more voids 920 and an outer surface of the first elongate member 102 may be about 1 to about 3 mm. In some embodiments, the first elongate member 102 and the second elongate member 104 include rounded edges.

Referring back to FIGS. 1 and 2, the second elongate member 104 includes a measurement window 106 configured to indicate a height of the tool 100 between the upper end 116 of the first elongate member 102 and the lower end 118 of the second elongate member 104. In some embodiments, the measurement window 106 is disposed on a front side 132 of the second elongate member 104. In some embodiments, the measurement window 106 is advantageously disposed about 4.0 to about 7.5 feet from the lower end 118 of the second elongate member 104 (e.g., the lower end of the tool 100) to provide a user of the tool 100 with easy viewing.

In some embodiments, the handle 108 is disposed vertically between the measurement window 106 and the lower end 118 of the second elongate member 104. The initial low position of the handle 108 allows a user to take tall vertical measurements, for example, about 8 to about 12 feet while minimizing raising of a user's hand, for example, above the user's shoulders, or above the user's head. In some embodiments, additional handles similar to the handle 108, such as a second handle, second and third handles, or the like, can be coupled to the first elongate member 102 at different positions along the first elongate member 102 to facilitate use by people of different heights or to facilitate ease of use for measuring different heights.

In some embodiments, the second elongate member 104 may include a clamp 122 to selectively lock or unlock the first elongate member 102 with respect to the second elongate member 104. In some embodiments, the clamp 122 is disposed between the measurement window 106 and the lower end 118 of the second elongate member 104. The first and second elongate members 102, 104 are advantageously slidingly engaged such that a user can squeeze the first and second elongate members 102, 104 together to temporarily clamp the first and second elongate members 102, 104 together to facilitate making a quick measurement or moving the tool 100 from place to place without the use of the clamp 122.

In some embodiments, the tool 100 includes a notepad assembly 150 coupled to the second elongate member 104 to facilitate recording measurement readings. The notepad assembly 150 generally comprises a stand for holding paper or a notepad. The notepad assembly 150 can be detachable from the tool 100 to facilitate use of the tool 100 without the notepad assembly 150. The clamp 122 and the notepad assembly 150 may be switchable between a right side of the tool 100 and the left-side of the tool 100 for right-handed or left-handed use.

In some embodiments, the second elongate member 104 includes a level indicator 130 to check if the tool 100 is level. In some embodiments, the level indicator 130 includes a suitable liquid disposed in a cavity, where the level indicator includes markings to designate when the tool 100 is level (e.g. perpendicular to a surface on which the tool 100 is disposed). In some embodiments, the level indicator 130 is disposed below the measurement window 106. However, the level indicator 130 may be disposed at any suitable position on the tool 100. In some embodiments, the level indicator 130 may comprise multiple cavities with a suitable liquid disposed in each cavity, for example, to provide a horizontal level reading and a vertical level reading.

Figure 3:
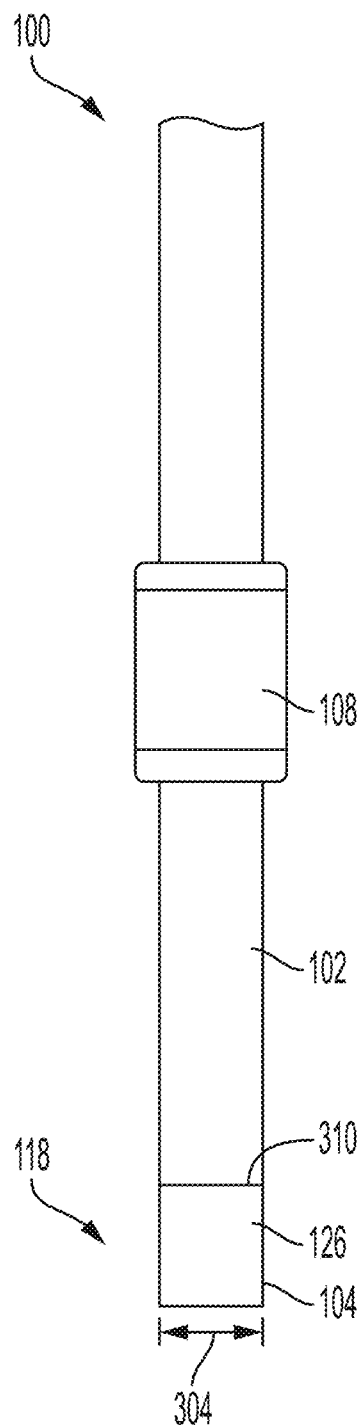
FIG. 3 depicts a back view of a lower portion of a tool for measuring a vertical height in accordance with some embodiments of the present disclosure.
Figure 4:
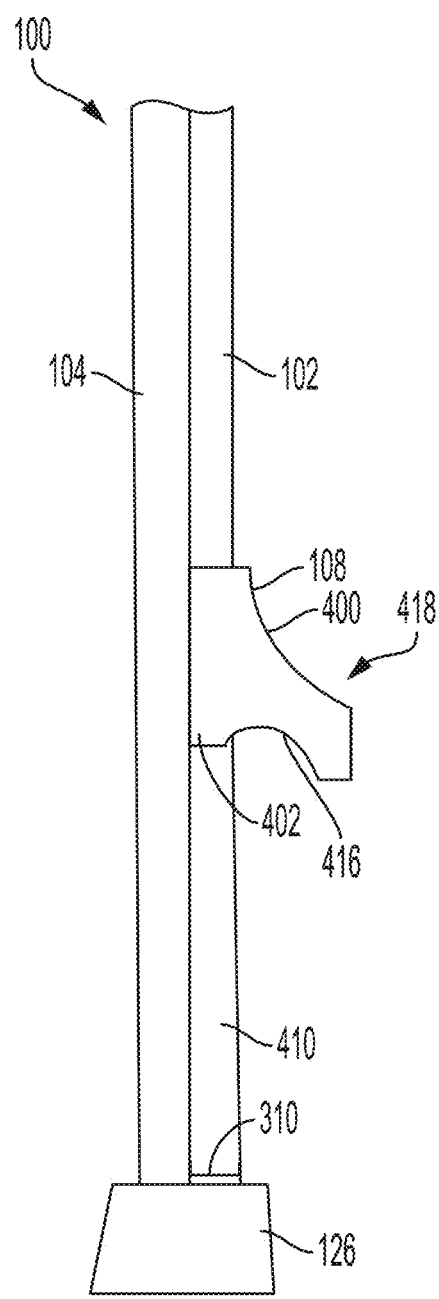
FIG. 4 depicts a right-side view of a lower portion of a tool for measuring a vertical height in accordance with some embodiments of the present disclosure.

FIG. 3 depicts a back view of a lower portion of a tool for measuring a vertical height in accordance with some embodiments of the present disclosure. FIG. 4 depicts a right-side view of a lower portion of a tool for measuring a vertical height in accordance with some embodiments of the present disclosure. In some embodiments, the handle 108 is adjustable along the elongate axis 140 of the first elongate member 102. The handle 108 may be removably coupled via any suitable manner. For example, the handle 108 may comprise a body 400 and wings 402 extending away from the body 400 to define a handle channel. The wings 402 may extend along sidewalls 410 of the first elongate member 102 so that the body 400 and wings 402 wrap around the first elongate member 102. The handle channel may be sized so that a width of the handle channel is similar to or slightly smaller than a width 304 of the first elongate member 102 so that the first elongate member 102 may be press-fit into the handle channel. The fit between the handle 108 and the first elongate member 102 may be snug enough fix the handle 108 to the first elongate member 102 while raising the first elongate member 102 while loose enough to pull the handle 108 off of the first elongate member 102 when needed to adjust a position of the handle 108 on the first elongate member 102. The position of handle 108 may advantageously be adjusted based on the heights of the walls the user may be working on.

Figure 11:
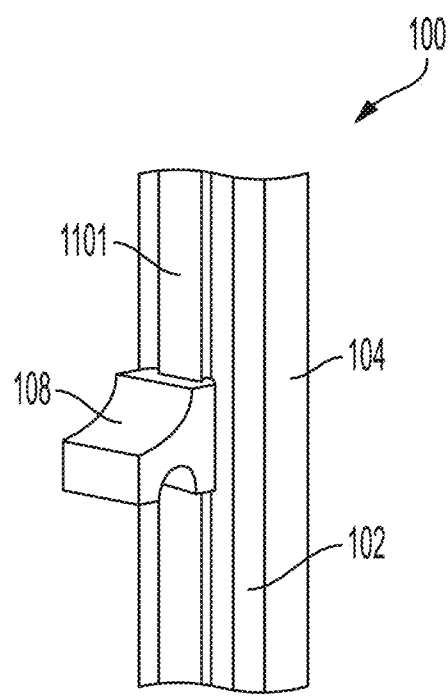
FIG. 11 depicts an isometric view of a portion of a tool for measuring a vertical height in accordance with some embodiments of the present disclosure.

In some embodiments, the handle 108 may be removably coupled to the first elongate member 102 via a magnetic coupling. For example, FIG. 11 depicts an isometric view of a portion of a tool 100 for measuring a vertical height in accordance with some embodiments of the present disclosure. In some embodiments, the handle 108 can be magnetically attached to the first elongate member 102 via magnetic strip 1101. The handle 108 may be made of a magnetic material, coupled to one or more magnets, or have one or more magnets embedded therein and may be configured to removably attach to the magnetic strip 1101 to control the position of the handle 108 on the first elongate member 102. The magnetic strip 1101 may be made of stainless steel or other suitable magnetic materials.

In some embodiments, the handle 108 is disposed about 8 inches to about 24 inches from a lower end 310 of the first elongate member 102. In some embodiments, a lower surface of the handle 108 includes a recess 416. The recess 416 may be curved to provide a smooth raising surface for a user. In some embodiments, an upper surface 418 of the handle 108 may be curved.

Figure 5:
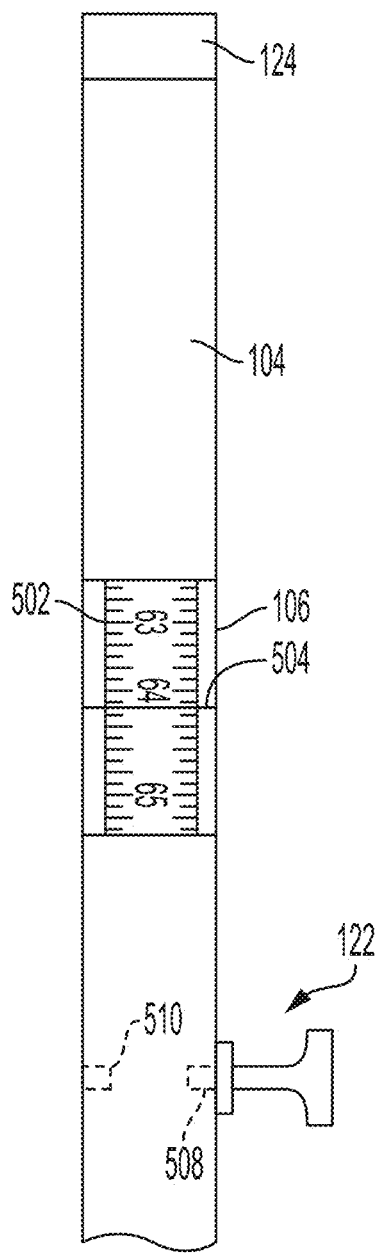
FIG. 5 depicts a front view of an upper portion of a tool for measuring a vertical height in accordance with some embodiments of the present disclosure.
Figure 6:
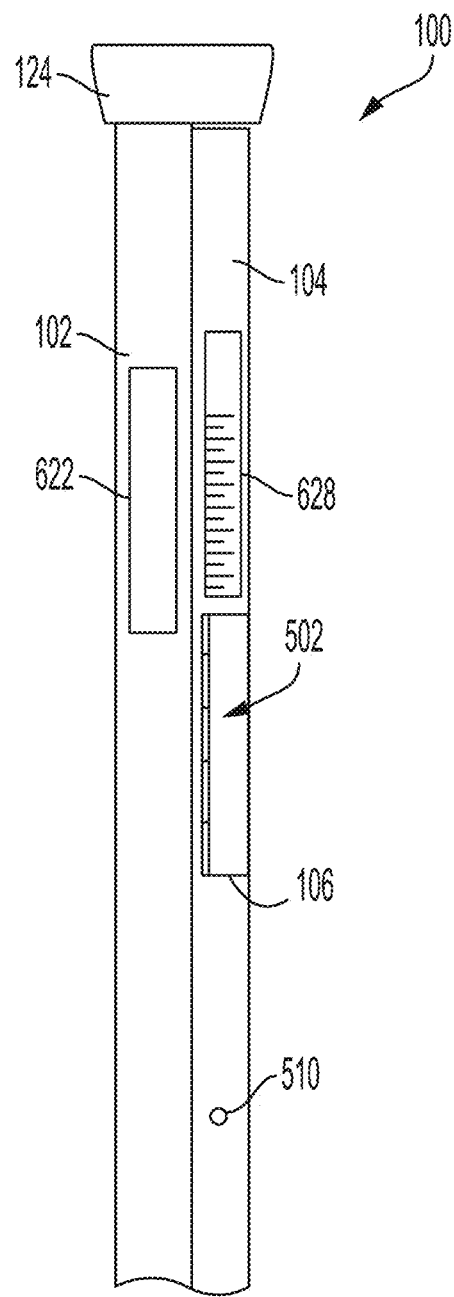
FIG. 6 depicts a left-side view of an upper portion of a tool for measuring a vertical height in accordance with the present disclosure.

FIG. 5 depicts a front view of an upper portion of a tool for measuring a vertical height in accordance with some embodiments of the present disclosure. FIG. 6 depicts a left-side view of an upper portion of a tool for measuring a vertical height in accordance with the present disclosure. In some embodiments, the first elongate member 102 includes a measurement tape 502. The measurement tape 502 includes measurement markings in any suitable units, for example, in metric, customary US system, or both. The measurement markings may be any suitable scale, such as down to $\frac{1}{32}$ of an inch, down to 1 mm, or the like. In some embodiments, the measurement tape 502 is formed or engraved in the channel 704, for example, the back surface 712 of the channel 704. In some embodiments, the measurement tape 502 is coupled to the back surface 712 of the channel 704.

The measurement tape 502 may be configured to show through the measurement window 106 of the second elongate member 104. In some embodiments, the measurement window 106 comprises a window with a marking 504, or indicator, to indicate a length, or height, of the tool 100. In some embodiments, the marking 504 can be a line, an arrow, or other suitable shape to facilitate reading the measurement tape 502 at an appropriate location to indicate a length of the tool 100. In some embodiments, the measurement window 106 comprises an opening through the second elongate member 104. In some embodiments, the measurement window 106 comprises a transparent material coupled to the second elongate member 104, where the marking 504 is disposed on the transparent material to indicate the height of the tool 100.

The measurement tape 502 may be configured to show measurement markings on multiple surfaces of the tool 100. In some embodiments, the marking 504 is disposed on sidewalls of the measurement window 106 or on the second elongate member 104 adjacent to the measurement window 106 to facilitate reading the measurement tape 502 at the correct location to indicate the height of the tool 100. In some embodiments, the tool 100 may include a measurement tape 622 on a sidewall of the first elongate member 102 and a marking, or indicator, on the second elongate member 104 to indicate a length, or height, of the tool 100. In some embodiments, the tool 100 may include both the measurement tape 502 and the measurement tape 622. In some embodiments, the second elongate member 104 includes the measurement tape 502 and the first elongate member 104 may include the marking or indicator to indicate a length or height of the tool 100.

In some embodiments, the second elongate member 104 includes an extended tape measure 628 on a sidewall of the second elongate member 104 that includes measurement markings that coordinate with the measurement markings of the measurement tape 502. For example, if the tool 100 is expanded such that the measurement markings of the measurement tape 502 extend beyond the measurement window 106, the height reading may be taken from the extended tape measure 628. In such embodiments, for example, the height reading may be taken from the extended tape measure 628 at a location aligned with the bottom of the first elongate member 102.

In some embodiments, the clamp 122 may be adjustable to selectively configure the clamp for right-hand use or left-hand use. For example, the second elongate member 104 may include a first threaded hole 508 and a second threaded hole 510 on a side of the second elongate member 104 opposite the first threaded hole.

Figure 8:
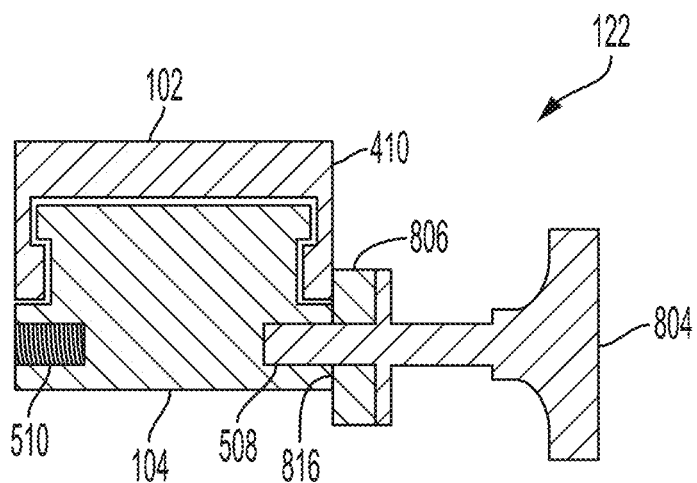
FIG. 8 depicts a cross-sectional top view of a tool for measuring a vertical height at a location of a clamp in accordance with some embodiments of the present disclosure.

FIG. 8 depicts a cross-sectional top view of a tool for measuring a vertical height at a location of a clamp 122 in accordance with some embodiments of the present disclosure. In some embodiments, an example of the clamp 122, as depicted in FIG. 8, includes a rotating portion 804 having a threaded end configured to interface with the first threaded hole 508 and the second threaded hole 510. Other types of suitable clamps may also be used. A washer 806 is disposed between a sidewall 816 of the second elongate member 104 and the rotating portion 804. When the rotating portion 804 is rotated to the locked position, as shown in FIG. 8, the washer 806 is pressed against the sidewall 816 and the sidewall 410 of the first elongate member 102, preventing the first elongate member 102 from sliding with respect to the second elongate member 104. The rotating portion 804 is rotated to the unlocked position, a gap forms between the washer 806 and the sidewall 816 and the sidewall 410, allowing the first elongate member 102 and the second elongate member 104 to slide with respect to each other.

In use, a user may place the foot 126 of the second elongate member 104 at a location where a vertical height measurement is desired. The user may then raise the first elongate member 102, for example, via the handle 108 until the head 124 contacts, for example, a horizontal stud, a ceiling, or the like. The user can then read a height measurement via the measurement window 106, record the height, and move the tool 100 to the next location where a vertical height measurement is desired. If needed, the user can use the clamp to lock the second elongate member 104 to the first elongate member 102 prior to recording the height. As such, the tool 100 may be used by a single user to quickly take and record measurements of required stud heights along one or more sections of a wall being constructed. The recorded measurements may then be taken to a cutting station to cut studs to the required heights. The tool 100 may facilitate taking vertical height measurements in a fraction of the time as compared to taking the same measurements with a measure tape, advantageously expediting construction.

While the foregoing is directed to embodiments of the present disclosure, other and further embodiments of the disclosure may be devised without departing from the basic scope thereof.

The invention claimed is:

1. A tool for measuring a length, comprising:
 a first elongate member having a measurement tape;
 a second elongate member slidingly coupled to the first elongate member via one or more channels interfacing with one or more protrusions, wherein the second elongate member includes a measurement window configured to facilitate reading of the measurement tape to indicate a length of the tool between opposing ends of the first elongate member and the second elongate member; and at least one of:
 a handle coupled to the first elongate member, wherein the handle is adjustable along the first elongate member, or
 an insert having a shape corresponding with the one or more protrusions disposed in each of the one or more channels and configured to facilitate smoother gliding between the first elongate member and the second elongate member.

2. The tool of claim 1, further comprising a clamp to selectively lock or unlock the first elongate member with respect to the second elongate member.

3. The tool of claim 1, wherein the measurement window comprises a window with a marking to indicate the length of the tool.

4. The tool of claim 1, wherein the first elongate member has an inverted T-shaped channel and the second elongate member is a T-shaped member that slidingly engages with the inverted T-shaped channel.

5. The tool of claim 1, wherein at least one of:
 the first elongate member has a length of about 4 to about 7 feet; or
 the second elongate member has a length of about 4 to about 7 feet.

6. The tool of claim 1, wherein the second elongate member includes a level indicator.

7. The tool of claim 1, wherein the first elongate member includes a head at one end of the first elongate member and the second elongate member includes a foot at an opposing end of the second elongate member.

8. A tool for measuring a length, comprising:
a first elongate member having one or more channels along an elongate axis; and
a second elongate member slidingly coupled to the first elongate member via one or more protrusions that extend through the one or more channels, wherein the second elongate member includes a measurement window on a front side of the second elongate member configured to facilitate reading of a measurement tape to indicate a length of the tool between opposing ends of the first elongate member and the second elongate member and a clamp to selectively lock or unlock the second elongate member with respect to the first elongate member, wherein the second elongate member includes a first hole and a second hole on a side of the second elongate member opposite the first hole, wherein the first hole and the second hole are selectively configured to receive the clamp for right-hand use or left-hand use.

9. The tool of claim 8, wherein the clamp is disposed between the measurement window and a lower end of the second elongate member.

10. The tool of claim 8, wherein the first elongate member has an inverted T-shaped channel, and the second elongate member has a T-shaped cross-section that slidingly engages with the inverted T-shaped channel.

11. The tool of claim 10, wherein the measurement tape is disposed in the inverted T-shaped channel and configured to show through the measurement window of the second elongate member.

12. The tool of claim 8, wherein the first hole comprises a first threaded hole and the second hole comprises a second threaded hole.

13. The tool of claim 8, wherein the one or more channels are two channels having a rounded cross-sectional shape.

14. A tool for measuring a length, comprising:
a first elongate member having one or more channels along an elongate axis;
a handle coupled to the first elongate member; and
a second elongate member slidingly coupled to the first elongate member via the one or more channels, wherein the second elongate member includes a measurement window disposed about 4.0 to about 7.5 feet from an end of the second elongate member and configured to facilitate reading of a measurement tape to indicate a length of the tool between opposing ends of the first elongate member and the second elongate member and a clamp to selectively lock or unlock the second elongate member with respect to the first elongate member, wherein the handle is disposed between the measurement window and a lower end of the second elongate member and configured to move the first elongate member with respect to the second elongate member.

15. The tool of claim 14, wherein the first elongate member includes a foot at one end of the first elongate member and the second elongate member includes a head at an opposing end of the second elongate member.

16. The tool of claim 14, wherein the handle is disposed about 8 inches to about 20 inches from a lower end of the first elongate member.

17. The tool of claim 14, wherein the first elongate member and the second elongate member are made of metal or a polymer.

18. The tool of claim 14, wherein the measurement window comprises an opening through the second elongate member.

* * * * *